United States Patent
Shimazu et al.

(10) Patent No.: US 7,071,360 B2
(45) Date of Patent: Jul. 4, 2006

(54) METHOD FOR EVAPORATING CYCLOHEXANONE OXIME

(75) Inventors: Yasumoto Shimazu, Niihama (JP);
Kanji Kuwahara, Niihama (JP);
Masaru Kitamura, Niihama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 923 days.

(21) Appl. No.: 10/105,321

(22) Filed: Mar. 26, 2002

(65) Prior Publication Data

US 2002/0143181 A1    Oct. 3, 2002

(30) Foreign Application Priority Data

Mar. 28, 2001    (JP) .................................... 2001-093361

(51) Int. Cl.
*C07C 249/00*    (2006.01)

(52) U.S. Cl. ........................................................ 564/264
(58) Field of Classification Search .................. 564/264
See application file for complete search history.

(56) References Cited

U.S. PATENT DOCUMENTS

| 3,210,338 A | 10/1965 | Huber et al. |
| 4,137,263 A | 1/1979 | Immel et al. |
| 4,268,440 A | 5/1981 | Werther et al. |

FOREIGN PATENT DOCUMENTS

| DE | 1126358 B | 3/1962 |
| EP | 0550965 B1 | 7/1993 |
| SE | 378290 A | 7/1964 |

*Primary Examiner*—Paul J. Killos
(74) *Attorney, Agent, or Firm*—Birch, Stewart, Kolasch & Birch, LLP

(57) ABSTRACT

A method is provided for evaporating cyclohexanone oxime in which cyclohexanone oxime is evaporated using a falling-film evaporator with wetting the evaporation surface of the evaporator well with the cyclohexanone oxime at a pressure of less than about 1060 Torr with a falling rate of the cyclohexanone oxime of about 170 kg/hour or more per one meter around the circumference of evaporation surface at the lowest part of the evaporator. In this method, the cyclohexanone oxime is evaporated efficiently with little decomposition thereof, while preventing the plugging of the pipes of the evaporator and continuously carrying out the operation of the evaporator for a long period of time.

5 Claims, 2 Drawing Sheets

METHOD FOR EVAPORATING CYCLOHEXANONE OXIME

FIELD OF THE INVENTION

The present invention relates to a method for evaporating cyclohexanone oxime, which may be used for producing ε-caprolactam. Specifically, the present invention relates to a method in which cyclohexanone oxime is evaporated smoothly with little decomposition thereof, which results in reducing bad influence upon the quality of ε-caprolactam produced by a gas phase Beckmann rearrangement reaction of cyclohexanone oxime.

BACKGROUND OF THE INVENTION

ε-caprolactam may be used as a monomer for producing Nylon-6, that is a raw material for producing fibers, engineering plastics and the like. ε-caprolactam may be produced by a process in which cyclohexanone oxime is evaporated and is then rearranged into ε-caprolactam in a gas phase Beckmann rearrangement reaction. The cyclohexanone oxime has to be evaporated in this process, and a lot of evaporation methods for the cyclohexanone oxime are known.

For example, JP-55-141467-A1 (corresponding to U.S. Pat. No. 4,268,440) discloses a method in which cyclohexanone oxime is evaporated, in the presence of an inert gas, in contact with a fluidized bed of inert solid particles such as silica sand. This method has problems such that a portion of the cyclohexanone oxime is decomposed in the fluidized bed and that much inert gas is needed.

JP-53-37641-A1 (corresponding to U.S. Pat. No. 4,137,263) discloses a method in which cyclohexanone oxime is evaporated in the presence of an inert gas at a super-atmospheric pressure of at least 300 Torr (i.e., at an absolute pressure of at least 1060 Torr) using a falling-film evaporator. This method also has problems such that the cyclohexanone oxime tends to remain in the evaporator and to generate crusts such as tar (or coke) due to the decomposition thereof, which may deteriorate the evaporation efficiency and may plug pipes of the evaporator.

SUMMARY OF THE INVENTION

One objective of the present invention is to provide a method for evaporating cyclohexanone oxime in which the cyclohexanone oxime is evaporated efficiently with little decomposition thereof without plugging the evaporator so as to extend a period of time for a continuous operation of the evaporator.

The present inventors have found that this object and other objects are achieved by a method in which cyclohexanone oxime is evaporated using a falling-film evaporator with wetting the evaporation surface of the evaporator well with the cyclohexanone oxime. In this method, the cyclohexanone oxime is evaporated efficiently with little decomposition thereof, while preventing the plugging of the pipes of the evaporator and continuously carrying out the operation of the evaporator for a long period of time. The present invention has accomplished based on these findings.

The present invention provides a method for evaporating cyclohexanone oxime using a falling-film evaporator at a pressure of less than about 1060 Torr with a falling rate of the cyclohexanone oxime of about 170 kg/hour or more per one meter around the circumference of evaporation surface at the lowest part of the evaporator.

DETAILED DESCRIPTION OF THE INVENTION

Figure 1:
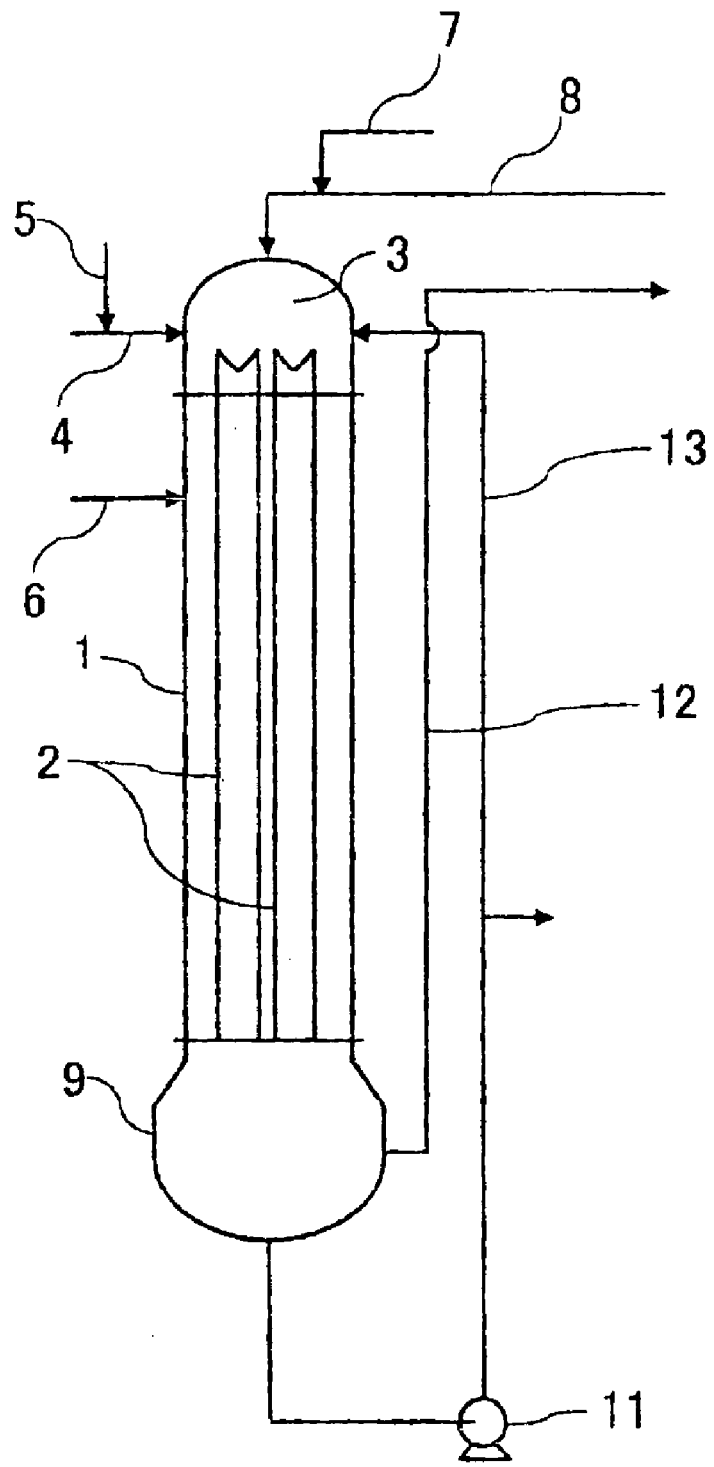
FIG. 1 illustrates a sectional view of a falling-film evaporator which can be utilized in the present invention.

In the present invention, cyclohexanone oxime is evaporated using a falling-film evaporator. The evaporation may be conducted with wetting the evaporation surface of the evaporator well with the cyclohexanone oxime. When the evaporation surface has a non-wet portion thereof, the cyclohexanone oxime may generate crusts such as tar in the evaporator.

In the present invention, the cyclohexanone oxime is preferably evaporated together with a solvent in the form of admixture thereof in order to reduce the heat decomposition of the cyclohexanone oxime. The solvent to be mixed and evaporated with cyclohexanone oxime is a solvent which has a boiling point lower than that of cyclohexanone oxime and is able to dissolve cyclohexanone oxime. Examples of the solvent include saturated alcohols having 1 to 8 carbon atoms such as methanol, ethanol, propanol, tertiary butanol, 1-hexanol and 1-octanol; aromatic hydrocarbons such as benzene and toluene. Among them, methanol and ethanol are preferred. The mixing ratio of cyclohexanone oxime to the solvent (cyclohexanone oxime:solvent) is preferably in the range of from 100:1 to 1:10, by weight.

When the evaporation surface of the evaporator is wet well with cyclohexanone oxime, a thin layer of the cyclohexanone oxime is formed on the whole evaporation surface of the evaporator. In the case that the mixture of a cyclohexanone oxime with a solvent is evaporated in the present invention, the above-described thin layer may be made from the mixture at the early period of the evaporation and then, at the latter period of the evaporation, may be made from substantially only the cyclohexanone oxime since the solvent is evaporated earlier than the cyclohexanone oxime.

The evaporation of cyclohexanone oxime is preferably conducted at a pressure of less than about 1060 Torr. When the pressure is about 1060 Torr or higher, cyclohexanone oxime tends to decompose. More preferably, cyclohexanone oxime is evaporated at a pressure of about 1000 Torr or lower. In the present invention, the cyclohexanone oxime which has not been evaporated and discharged from the falling-film evaporator may be forced to be circulated in the evaporator.

In order to maintain the whole evaporation surface of the falling-film evaporator wet with the cyclohexanone oxime, it is preferred that the cyclohexanone oxime is suppled into the evaporator with a falling rate of the cyclohexanone oxime of about 170 kg/hour (in terms of cyclohexanone oxime when the mixture thereof is supplied) or more per one meter around the circumference of evaporation surface at the lowest part of the evaporator. When the falling rate is less than about 170 kg/hour per one meter around the circumference of evaporation surface at the lowest part of the evaporator, there may be a non-wet portion of the evaporation surface.

The falling rate of the cyclohexanone oxime is preferably from about 170 kg/hour to about 1700 kg/hour, and more preferably from about 340 kg/hour to about 680 kg/hour, per one meter around the circumference of evaporation surface.

The evaporation of cyclohexanone oxime may be conducted in the presence of an inert gas and may be carried out at a temperature of from about 130° C. to about 170° C.

For reference, the present invention is described using FIG. 1, which should not be construed as a limitation upon the scope of the present invention.

FIG. 1 illustrates a sectional view of one example of a falling-film evaporator, which can be utilized in the present invention. Falling-film evaporator 1 is a multiple-tube falling-film evaporation column. From supplying part 3 at the top of the column, a mixture of a cyclohexanone oxime with a solvent may be supplied into pipes 2, 2. The mixture falls down, while forming a thin layer of the mixture on the surface inside the pipes. The outside of pipes 2, 2 is heated by a heat source such as steam, which is fed into the column from heat source feeding pipe 6, so that the mixture is evaporated by the heating.

The cyclohexanone oxime is introduced to supplying part 3 through oxime supplying pipe 4. During the supplying, the solvent may be introduced through solvent supplying pipe 5 so as to prepare the mixture of the cyclohexanone oxime with the solvent. Alternatively, the solvent may be introduced to supplying part 3 through a supplying pipe (which is not illustrated) other than solvent supplying pipe 5 so as to prepare the mixture in supplying part 3.

An inert gas and a gas of a solvent may be introduced through gas supplying pipes 7, 8 and may be fed into supplying part 3 in the form of admixture thereof. Examples of the inert gas include nitrogen gas. Examples of the gas of the solvent include gases of the above-described solvents which can be used together with the cyclohexanone oxime. Preferably, a methanol gas is utilized.

By the presence of the solvent and/or the solvent gas, the decomposition of the cyclohexanone oxime tends to be reduced. In the case that an alcohol is utilized as the solvent and/or the solvent gas in the evaporation, the solvent is introduced together with the cyclohexanone oxime into a gas phase Beckmann rearrangement reaction system of the cyclohexanone oxime (for example, into a fluidized bed thereof), and provides a high yield of ε-caprolactam.

The mixture of the cyclohexanone oxime with the solvent supplied into supplying part 3 may fall down together with the inert gas and the solvent gas inside pipes 2, 2. The entire evaporation surface, which is inside pipes 2, 2, is wet with the at least cyclohexanone oxime. When there is non-wet portion on the evaporation surface, a cyclohexanone oxime may remain at the portion to form crusts such as tar, which results in plugging pipes 2, 2.

The evaporation of the mixture is preferably conducted at a pressure of less than about 1060 Torr with a falling rate of the cyclohexanone oxime of about 170 kg/hour or more per one meter around the circumference of evaporation surface at the lowest part of the evaporator.

The evaporated mixture gas is exhausted from column bottom 9 and is fed into a reaction step through supplying pipe 12 for introducing a raw material of the reaction. On the other hand, the cyclohexanone oxime which has not been evaporated inside pipes 2,2 remaining at column bottom 9 may be discharged from column bottom 9 and be fed by pump 11 through circulating pipe 13 into supplying part 3. In such a way, the un-evaporated mixture may be forced to be circulated in falling-film evaporator 1. The circulating rate of the un-evaporated mixture may correspond to the falling rate of the cyclohexanone oxime mixture at the lowest part of pipes 2,2 in the evaporator.

A portion of the un-evaporated mixture may be discharged through circulating pipe 13 in order to adjust the composition of the un-evaporated mixture. This discharged mixture may be sent into a second evaporator (such as an evaporator with scraping blades and a distillation column) and may be separated from impurities such as tar therein, so that the cyclohexanone oxime contained therein can be reused for the evaporation.

In the above description, the mixture of the cyclohexanone oxime with the solvent may be introduced into pipes 2,2 and a thin layer thereof may be formed inside the pipes. Alternatively, a heat source such as steam may be introduced in pipes 2,2 and the mixture of the cyclohexanone oxime with the solvent may be allowed to fall down outside the pipes, so that the thin layer of the mixture is formed outside the pipes.

In the method for evaporation of the present invention, a cyclohexanone oxime may be evaporated together with a solvent, as described above, or may be evaporated alone.

In accordance with the present invention, cyclohexanone oxime is evaporated smoothly and efficiently using a falling-film evaporator with little decomposition thereof, while suppressing the formation of tar and prolonging the operation of the evaporator for a long period of time. Also, by evaporating a cyclohexanone oxime together with a solvent, heat decomposition of the cyclohexanone oxime can be reduced.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2001-93361 filed on Mar. 28, 2001, indicating specification, claims, drawings and summary, are incorporated herein by reference in their entirety.

EXAMPLES

The present invention is described by the following Examples, which are not intended to limit the scope of the invention in any way.

Example 1

Using the same type of a falling-film evaporator as shown in FIG. 1 except to have four cylindrical pipes for introducing cyclohexanone oxime therein, was evaporated cyclohexanone oxime in a circulation system together with methanol as a solvent while introducing a nitrogen gas as an inert gas together with a methanol gas. The falling-film evaporator has four cylindrical pipes, each having a diameter of 50 mm and a length of 6 m. The evaporation was conducted under the conditions as follows:

Rate of supplying the cyclohexanone oxime: 250 kg/hour

Rate of supplying the methanol: 50 kg/hour

Rate of introducing the methanol gas: 400 kg/hour

Rate of introducing the nitrogen gas: 50 kg/hour

Evaporation temperature: 140° C.–160° C.

The evaporation pressure: 950 Torr or lower

Circulating rate of the un-evaporated mixture: 250 kg/hour

Falling rate of the cyclohexanone oxime mixture: 398 kg/hour (per one meter around the circumference of the evaporation surface at the lowest part of pipe 2)

The evaporation was carried out continuously. After 60 days of the evaporation, each of pipes 2 was not plugged. The amounts of by-products (such as cyclohexanone, which was generated from cyclohexanone oxime) in the evaporated cyclohexanone oxime in pipe 12 and the remaining cyclohexanone oxime in pipe 13 were measured with gas chromatography. As a result, the decomposition ratio of the cyclohexanone oxime was 0.12%.

Comparative Example 1

Figure 2:
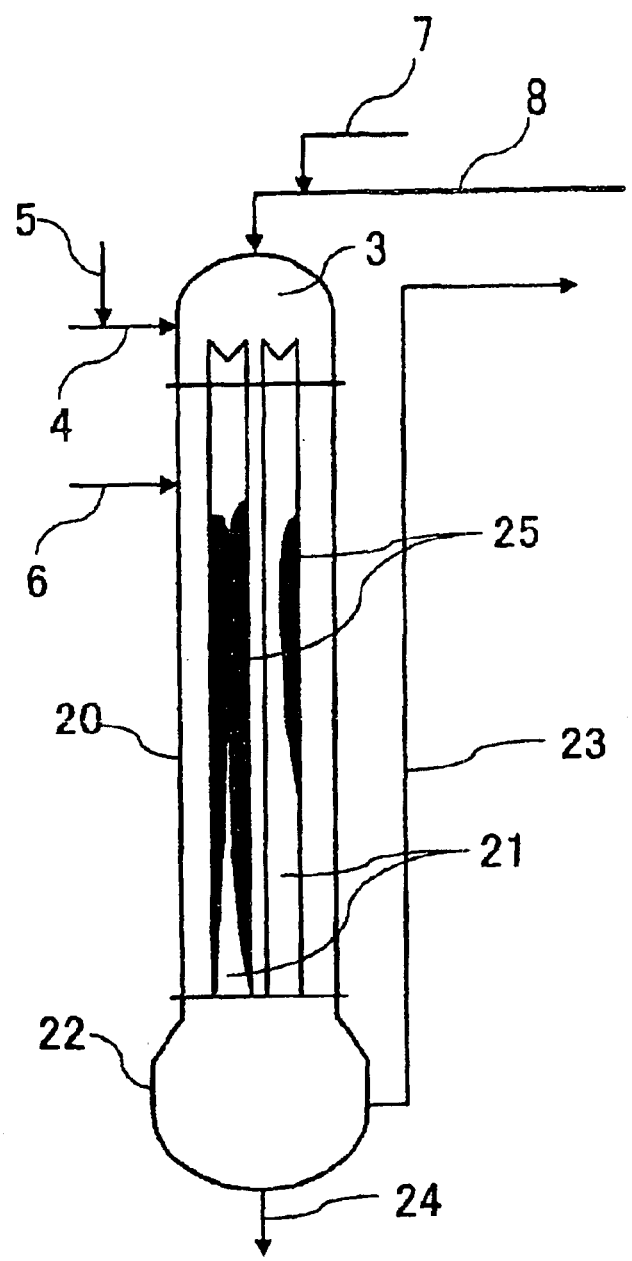
FIG. 2 illustrates a sectional view of another falling-film evaporator.

Using falling-film evaporator 20 shown in FIG. 2, was evaporated cyclohexanone oxime together with methanol, while introducing a nitrogen gas and a methanol gas, by one time introducing the mixture of the cyclohexanone oxime without circulating the mixture in a perfect evaporation system. The falling-film evaporator has no circulation system and has twenty-eight cylindrical pipes 21, each having a diameter of 50 mm and a length of 6 m. From bottom part 22 of falling-film evaporator 20, an evaporated mixture gas of the cyclohexanone oxime was exhausted through supplying pipe 23 for introducing a raw material of the reaction. A tar component generated from the cyclohexanone oxime was discharged through discharge pipe 24. Other than those parts such as the above-described pipes, falling-film evaporator 20 has the same parts as those of falling-film evaporator 1.

The evaporation was conducted under the same conditions (for example, the rates of supplying the cyclohexanone oxime, the methanol, the methanol gas and the nitrogen gas; the evaporation temperature; and the evaporation pressure) as in Example 1. The falling rate of the cyclohexanone oxime mixture was 0.5 kg/hour per one meter around the circumference of the evaporation surface at the lowest part of pipe 21.

The evaporation was carried out continuously. After 10 days of the evaporation, tar component 25 was observed and pipes 21 were plugged with the tar components.

What is claimed is:

1. A method for evaporating cyclohexanone oxime using a falling-film evaporator at a pressure of less than about 1060 Torr with a falling rate of the cyclohexanone oxime of about 170 kg/hour or more per one meter around the circumference of evaporation surface at the lowest part of the evaporator.

2. The method according to claim 1, wherein the cyclohexanone oxime is evaporated together with a solvent in the form of admixture thereof.

3. The method according to claim 2, wherein the solvent is an alcohol.

4. The method according to claim 1 or 2, wherein the cyclohexanone oxime which has not been evaporated is circulated in the falling-film evaporator.

5. The method according to claim 1 or 2, wherein the cyclohexanone oxime is evaporated in the presence of an inert gas.

* * * * *